United States Patent [19]

Satomura et al.

[11] Patent Number: 5,780,247

[45] Date of Patent: *Jul. 14, 1998

[54] PROCESS FOR SEPARATING AND MEASURING TRACE COMPONENTS

[75] Inventors: Shinji Satomura, Osaka; Kenji Nakamura, Toyonaka; Shuji Matuura, Kawanishi, all of Japan

[73] Assignee: Wako Pure Chemical Industries, Ltd., Osaka, Japan

[*] Notice: The term of this patent shall not extend beyond the expiration date of Pat. Nos. 5,571,729 and 5,591,589.

[21] Appl. No.: 488,009

[22] Filed: Jun. 7, 1995

Related U.S. Application Data

[63] Continuation of Ser. No. 133,782, Oct. 8, 1993, abandoned, which is a continuation of Ser. No. 640,768, Jan. 4, 1991, abandoned.

[30] Foreign Application Priority Data

Jan. 9, 1990 [JP] Japan ................................. 2-002170
Jan. 26, 1990 [JP] Japan ................................. 2-016694

[51] Int. Cl.$^6$ ................................................. G01N 33/574
[52] U.S. Cl. .............................. 435/7.23; 435/7.1; 435/7.4; 435/7.9; 435/971; 435/973; 436/161; 436/514; 436/536; 436/538; 436/541; 436/824; 436/827; 422/68.1; 422/70; 530/412; 530/413; 530/416; 530/417
[58] Field of Search ........................ 435/7.1, 7.23, 435/7.4, 7.9, 971, 973; 436/161, 541, 824, 827, 514, 538; 422/68.1, 70; 530/412, 413, 416, 417; 210/660, 661, 662, 669

[56] References Cited

U.S. PATENT DOCUMENTS

| 4,493,793 | 1/1985 | Chu ................................. 260/112 |
| 4,624,916 | 11/1986 | Shah et al. ....................... 435/7.4 |
| 4,681,842 | 7/1987 | Rosalki ............................. 435/21 |
| 4,939,092 | 7/1990 | Naujoks et al. ................... 435/7.4 |
| 5,571,729 | 11/1996 | Satomura et al. ................. 436/541 |
| 5,591,589 | 1/1997 | Katoh et al. ...................... 435/7.1 |

FOREIGN PATENT DOCUMENTS

| 0357869 | 3/1990 | European Pat. Off. |
| 2951678 | 7/1980 | Germany . |
| 0185169 | 8/1987 | Japan ............................. 435/973 |

OTHER PUBLICATIONS

Schlabach et al., Anal. Chem. vol. 52, pp. 729–733 (1980) "Determination of Serum Isoenzyme Activity Profiles by High Performance Liquid Chromatography".

Wu et al., J. Immunol. Meth. vol. 124, pp. 165–169 (1989) "The identification of antigens in antibody/antigen complexes using high performance liquid chromatography".

Omichi et al., Anal. Biochem. vol. 168, pp. 332–336 (1988) "Separation of Human Salivary α-Amylase Isozymes by High-Performance Liquid Chromatography with a Continuous Monitor System of the Activity".

Kennedy et al., J. Biotechnol., 9, 83 (1989).

Kawaguchi et al Journal of Chromatography, 374 (1986) 45–50, "Automatic Analysis of Serum Lactate Dehydrogenase Isoenzymes by High-Performance Ion-Exchange Chromatography".

(List continued on next page.)

Primary Examiner—Susan Wolski
Attorney, Agent, or Firm—Armstrong, Westerman, Hattori, McLeland & Naughton

[57] ABSTRACT

Two or more analytes having the same action, or having different actions in spite of their similar structures, or two or more analytes having the same action and the same detectable chemical characteristics, in samples derived from living bodies, etc., can be measured rapidly and easily by forming one or more complexes with one or more affinity substances, separating the complexes by using high pressure liquid chromatography, followed by measurement of the amount of an affinity substance or one of the analytes.

9 Claims, 5 Drawing Sheets

OTHER PUBLICATIONS

Kawaguchi et al Journal of Chromatograhy. 378 (1986) 456–461. "Rapid Analysis of Serum Lactate Dehydrogenase Isoenzymes by High–Performance Ion–Exchange Chromatography".
Carty et al J. Chromatography 447 (1988) 279–288.
Karande et al J. Imm. Methods 99 (1987) 173–177.
Clark et al in *Enzyme Immunoassay* Chapter 8 pp. 167–179 (1987).
Doyle et al ASM News 55 (1989) pp. 655–658.
Ling et al in *Practical Immunoassay* pp. 199–215 (1984).
Burchiel Met Enz. 121 (1986) pp. 596–615.
Holmskou–Nielson Immunolosy 51 (1984) pp. 809–814.
Freytag et al., *Clinical Chem.*, 30, 1494 (1984).

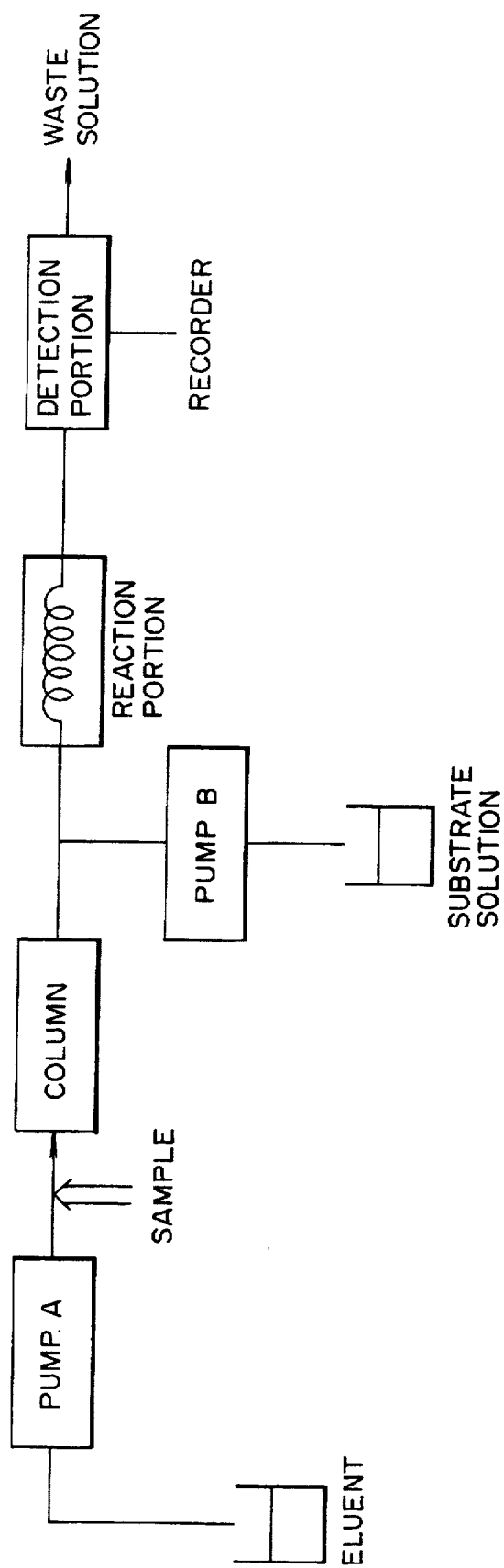
F I G. 2

PROCESS FOR SEPARATING AND MEASURING TRACE COMPONENTS

This application is a continuation of application Ser. No. 08/133,782, filed Oct. 8, 1993, now abandoned, which was a continuation of application Ser. No. 07/640,768, filed Jan. 4, 1991, now abandoned.

BACKGROUND OF THE INVENTION

This invention relates to a process for separating and measuring two or more analytes to be measured having the same action, or having different actions in spite of their similar structures, or two or more analytes to be measured having the same action and the same detectable chemical characteristics, in samples derived from living bodies, for example, body fluids such as serum, blood, plasma and urine, lymphocyte, hemocyte, and various cells, rapidly and easily with higher precision on the basis of chemical and/or physical properties of the analytes.

Among trace components contained in samples derived from living bodies, there are trace components which have the same action but have different chemical and/or physical properties, and trace components which have similar structures but have different actions. The former includes, for example, physiologically active substances such as enzymes (isozymes) different in the structure of their protein portion or sugar chain portion, and hormones different in sugar chain structure. The latter includes, for example, physiologically active substances such as steroid hormones and other hormones, e.g., thyroid stimulating hormone (TSH), follicle stimulating hormone (FSH), human chorionic gonadotropin (hCG), etc. It is well known that a clinically effective indication can be obtained if the amounts of these trace components in a sample can be individually separated and measured on the basis of their various properties.

As a conventional method for separating and measuring these trace components, there can be exemplified electrophoretic methods, immunoassay methods, and methods utilizing antibody or inhibition of enzymatic activity by use of an inhibitor. These methods, however, are disadvantageous, for example, in that a long time is required for measurement and that the quantitativeness is not sufficient. Therefore, they are not always practical.

On the other hand, as a method free from such problems, there have been proposed methods in which isozymes of lactate dehydrogenase are separated and measured by a high pressure liquid chromatography (HPLC) using a column packed with a packing for ion-exchange chromatography (J. Chromatogr., 374, 45–50 (1986) and J. Chromatogr., 378, 456–461 (1986)). These methods, however, are also disadvantageous, for example, in that substances which can be separated and measured by the methods are limited to some extent, and that measurement conditions for separation should be determined depending on analytes to be measured. Therefore, they are not always good methods, and there has been a desire to seek further improvement in them.

SUMMARY OF THE INVENTION

This invention was made in consideration of such conditions and is intended to provide a process which makes it possible to separate and measure two or more analytes to be measured having the same action or having different actions in spite of their similar structures, or two or more analytes to be measured having the same action and the same detectable chemical characteristic, in for example, samples derived from living bodies, rapidly and easily with high precision on the basis of chemical and/or physical properties of the analytes.

This invention provides a separating and measuring process which comprises mixing a sample containing two or more analytes to be measured having the same action or having different actions in spite of their similar structures (hereinafter abbreviated merely as "analytes A") with a substance having affinity for all of the analytes A and has in itself a property detectable by some method or has been labeled with a substance detectable by some method (hereinafter abbreviated as "affinity substance $\alpha$") and a substance which has affinity for at least one of the analytes A but does not bind to at least one of the other analytes A (hereinafter abbreviated as "affinity substance $\beta$"); reacting the analytes A with the affinity substance $\alpha$ and the affinity substance $\beta$; separating a complex of analyte(s) A and the affinity substance $\alpha$ (hereinafter abbreviated as "complex I"), a complex of analyte(s) A, the affinity substance $\alpha$ and the affinity substance $\beta$ (hereinafter abbreviated as "complex II") and free affinity substance $\alpha$ from one another by a high pressure liquid chromatography; measuring the amount of the affinity substance $\alpha$ in the complex I and/or the amount of the affinity substance $\alpha$ in the complex II; and thereby measuring the amount of any of the analytes A in the sample. (This process is hereinafter abbreviated as "process-1".)

This invention further provides a separating and measuring process which comprises mixing a sample containing two or more analytes to be measured having the same action and the same detectable chemical characteristic (hereinafter abbreviated merely as "analytes B") with a substance which has affinity for at least one of the analytes B but does not bind to at least one of the other analytes B (hereinafter abbreviated merely as "affinity substance $\gamma$"); reacting the analytes B with the affinity substance $\gamma$; separating a complex of analyte(s) B and the affinity substance $\gamma$ (hereinafter abbreviated merely as "complex III") from free analyte(s) B by a high pressure liquid chromatography; measuring the amount of analyte B in the complex III and/or the amount of the free analyte(s) B; and thereby measuring the amount of any of the analytes B in the sample. (This process is hereinafter abbreviated as "process-2".)

BRIEF DESCRIPTION OF THE DRAWINGS

FIG. 2 is a schematic diagram showing the outline of a HPLC system used in Examples 1, 2, 3, 4, 5 and 6 and Comparative Example 1.

DESCRIPTION OF THE PREFERRED EMBODIMENTS

Figure 4:
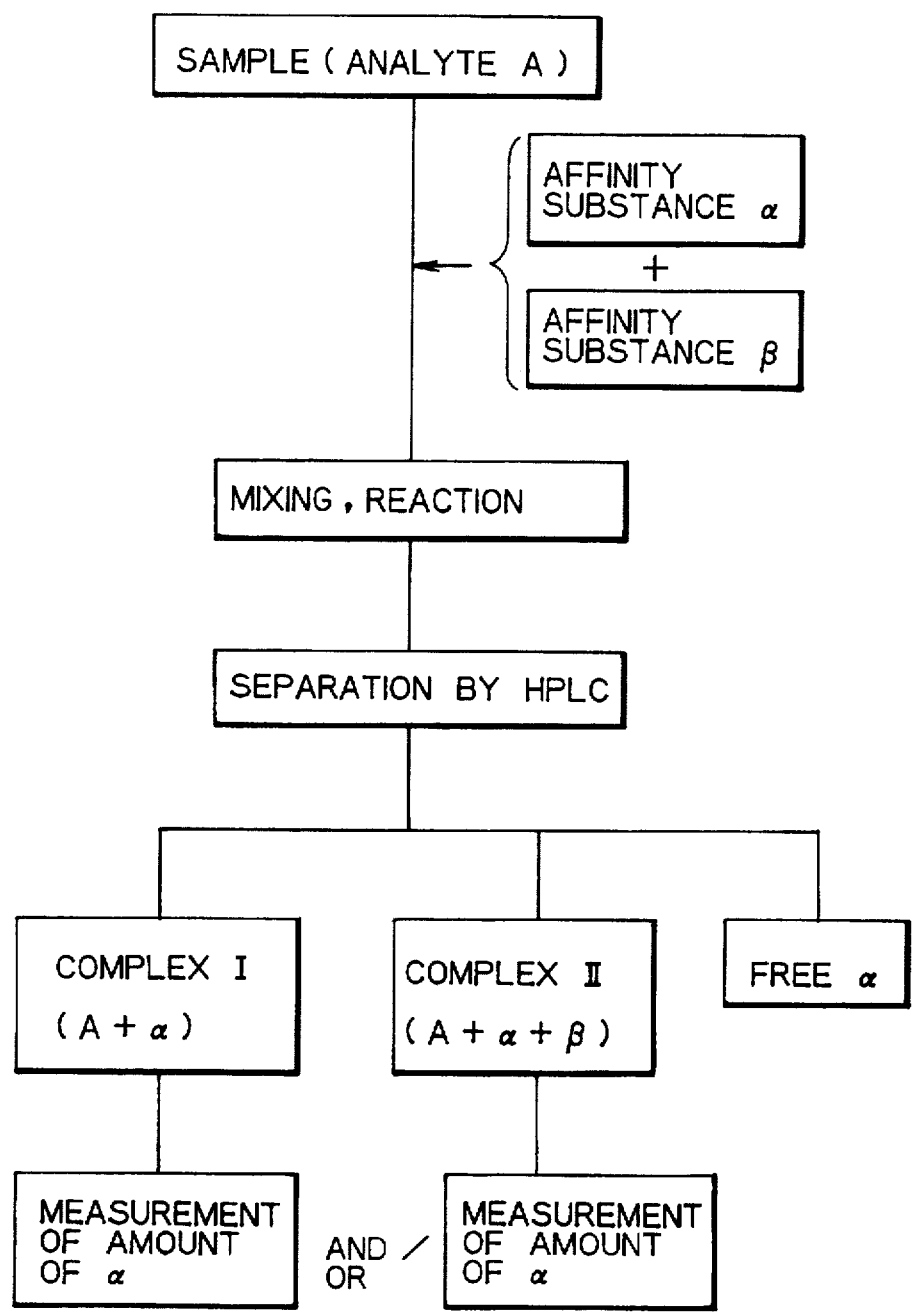
FIGS. 4 and 5 are flow sheets explaining processes of the present invention.

The process-1 of this invention is practised, for example, as shown in FIG. 4, as follows.

First, a sample derived from a living body which contains analytes A is reacted with an affinity substance $\alpha$ and an affinity substance $\beta$, if necessary, by their addition to and mixing in a suitable buffer solution, to form a complex I and a complex II. Then, the complex I, the complex II and free affinity substance $\alpha$ are separated from one another by a HPLC using a column packed with a predetermined packing. Subsequently, the amount of the affinity substance $\alpha$ contained in the separated complex I or the amount of the affinity substance $\alpha$ contained in the separated complex II, or both, are determined by a measuring method suitable for properties of the affinity substance α. Thus, the amount of any of the analytes A in the sample can be measured.

Analytes A which can be measured by the process-1 of this invention are not critical so long as they satisfy the following conditions i) and ii). i) There exists a substance which binds to all analytes A in the sample and which has in itself a property detectable by some method or can be labeled with a substance detectable by some method (hereinafter abbreviated as "detectable substance"). ii) There exists a substance which can form a stable complex with at least one of the analytes A by a high affinity between the substance and the analyte(s) A but does not bind to at least one of the other analytes A. Typical examples of the analytes A are enzymes, physiologically active substances, tumor associated antigens, substances having a sugar chain, etc. which are contained in samples derived from living bodies, for example, body fluids such as serum, blood, plasma, urine and the like, lymphocytes, hemocytes, and various cells. More specific examples of the analytes A are preferably enzymes such as amylase, alkaline phosphatase, acid phosphatase, γ-glutamyltransferase (γ-GTP), lipase, creatine kinase (CK), lactate dehydrogenase (LDH), glutamic-oxaloacetic transaminase (GOT), glutamic-pyruvic transaminase (GPT), renin, protein kinases, tyrosine kinase, and the like; physiologically active substances such as steroid hormones, human chorionic gonadotropin (hCG), prolactin, thyroid stimulating hormone (TSH), luteinizing hormone (LH), and the like; and tumor associated antigens such as prostate gland specific antigen (PSA), $\alpha_2$-macroglobulin, carcinoembryonic antigen (CEA), α-fetoprotein, and the like.

The affinity substance a used in the process-1 of this invention is not critical so long as it binds to all of the analytes A and it has in itself a property detectable by some method or has been labeled with a detectable substance. Specific examples of substance having affinity for all of the analytes A which can be used as the affinity substance α or for preparation of the affinity substance α are antibodies against specific partial structures or antigenic determinants of substances having antigenicity (including haptens); lectins having affinity for sugar chains having a specific structure, such as concanavalin A, *Lens culinaris* lectin, *Phaseolus vulgaris* lectin, *Datura stramonium* agglutinin lectin, *Aleuria aurantia* lectin, *Ricinus communis* lectin, *Arachis hypogaea* lectin, *Triticum vulgaris* lectin, and the like; and inhibitors for enzymes such as amylase, creatin kinase (CK), glutamic-oxaloacetic transaminase (GOT) and the like. Preferable specific examples of the affinity substance α are labeled products obtained by labeling these substances with a detectable substance. The detectable substance includes, for example, enzymes such as alkaline phosphatases, β-galactosidase, peroxidase, microperoxidase, glucose oxidase, glucose-6-phosphate dehydrogenase, malate dehydrogenase, luciferase, etc., which are used, for example, in enzyme immunoassay (ELA); radioisotopes such as $^{99m}$Tc, $^{131}$I, $^{125}$I, $^{14}$C, $^{3}$H, etc., which are used, for example, in radioimmunoassay (RIA); substances which can emit fluorescence, such as fluorescein, dancyl residue, fluorescamine, coumarin, naphthylamine, derivatives thereof, etc., which are used, for example, in fluoroimmunoassay (FIA); luminescent substances such as luciferin, isoluminol, luminol, bis(2,4,6-trifluorophenyl) oxalate, etc.; substances which can absorb ultraviolet light, such as phenol, naphthol, anthracene, derivatives thereof, etc.; and substances having properties as spin, which are represented by compounds having an oxyl group, such as 4-amino-2,2,6,6-tetramethylpiperidin-1-oxyl, 3-amino-2,2, 5,5-tetramethylpyrrolidin-1-oxyl, 2,6-di-t-butyl-α-(3,5-di-t-butyl-4-oxo-2,5-cyclohexadien-1-ylidene)-p-tolyloxyl, etc. Needless to say, the detectable substance is not limited to these listed substances.

As a method for preparing the affinity substance α by labeling the above-exemplified substance with the above-exemplified detectable substance, there can be exemplified all of conventional lableing methods which are generally employed, for example, in conventional EIA, RIA and FIA (e.g. Yuichi Yamamura "Ikagaku Jikken Koza Vol. 8" 1st ed., NAKAYAMA-SHOTEN Ltd., 1971; Akira Kawao "Zusetsu Keiko Kotai" 1st ed., Soft Science Inc., 1983; and Eiji Ishikawa,Tadashi Kawai and Kiyoshi Miyai "Koso Men-eki Sokuteiho" 2nd ed., IGAKU-SHOIN Ltd., 1982). The preparation may be carried out according to these methods. Needless to say, as a method for the labeling, there may be employed a conventional method utilizing the reaction of avidin (or streptoavidin) with biotin.

As the affinity substance α used in the process-1 of this invention, there can be exemplified, besides the substances thus labeled with the detectable substances, substances which themselves have a property detectable by some method. As the property detectable by some method of the affinity substance α used in the process-1 of this invention, there can be exemplified enzyme activities, fluorescence-emitting properties, luminescence-emitting properties, and ultraviolet-light-absorbing properties.

The affinity substance β used in the process-1 of this invention is not critical, so long as it can form a stable complex with at least one of the analytes A by a high affinity between the affinity substance β and the analyte(s) A but does not bind to at least one of the other analytes A. Preferable specific examples of the affinity substance β are specific antibodies against specific partial structures or antigenic determinants of substances having antigenicity (including haptens); lectins having affinity for sugar chains having a specific structure, such as concanavalin A, *Lens culinaris* lectin, *Phaseolus vulgaris* lectin, *Datura stramonium* agglutinin lectin, *Aleuria aurantia* lectin, *Ricinus communis* lectin, *Arachis hypogaea* lectin, *Triticum vulgaris* lectin, and the like; and specified inhibitors for amylase, creatin kinase (CK), glutamicoxaloacetic transaminase (GOT) and the like.

If necessary, the affinity substance β may be labeled with the detectable substance described above for the affinity substance α, by the above-exemplified method. In this case, when the affinity substance β is labeled with the same detectable substance as the affinity substance α has, the detection sensitivity for the complex II is enhanced, resulting in easy detection. However, when the process-1 of this invention is practised by use of the labeled affinity substance β, free affinity substance β should, of course, be separable from the complex I and the complex II by HPLC.

More specific examples of combinations of the above analyte A and affinity substance α and β are as shown in Table 1.

TABLE 1

| Analyte A | Affinity substance α | Affinity substance β |
|---|---|---|
| Substance having antigenecity (including haptens) | Antibodies | Antibodies or Lectins |
| Sugar chains | Lectins | " |

TABLE 1-continued

| Analyte A | Affinity substance α | Affinity substance β |
|---|---|---|
| Inhibitors | Proteases | " |
| Proteases | Inhibitors | " |
| Antibodies | Antigen against antibodies as analytes | " |
| Nucleic acids | Complementary polynucleotides | Antibodies or complementary polynucleotides |

In the process-1 of this invention, the reaction conditions for reacting the analytes A with the affinity substance α and the affinity substance β to form the complex I and the complex II are not critical so long as the reaction conditions neither inhibit the formation of the complex I and the complex II nor change properties of the analytes A, the affinity substance α and the affinity substance β. The reaction is carried out usually under reaction conditions employed for forming a complex or the like in a conventional method, for example, EIA, RIA, FIA or affinity chromatography. For example, when a buffer solution is used in the reaction, as the buffer and other reagents, those used in the above conventional methods may be properly chosen.

In the process-1 of this invention, the concentrations of the affinity substance α and the affinity substance β used for forming the complex I and the complex II are not critical and may be properly determined depending on values at which the limit of measurement of the analytes A and the measurement sensitivity for the analytes A are set, respectively. As each of the affinity substance α and the affinity substance β, employment of one substance is usually sufficient, though if necessary, a combination of two or more substances may be used. In this case, when there is used, for example, a combination of two or more affinity substances α which bind to different sites on analytes A, respectively, and two or more affinity substances β which bind to different sites on optional analyte(s) A, respectively, the molecular weights of the complex I and the complex II are consequently increased, and their isoelectric points are also varied in some cases. Therefore, the separation of the complex I, the complex II and free affinity substance α becomes easier, so that the precision of measurement can be improved. In the case of, for example, analytes A which are in the form of a mixture of X, Y and Z, combined use of, for instance, an affinity substance β for X and an affinity substance β for Y makes it possible to separate and measure X, Y and Z at the same time.

In the process-1 of this invention, although the pH at the reaction is not critical so long as it does not inhibit the formation of the complex I and the complex II, it is usually 2 to 10, preferably 5 to 9. Although the temperature at the reaction is also not critical so long as it does not inhibit the formation of the complex I and the complex II, it is usually 0° to 70° C., preferably 20° to 40° C. As to the reaction time, since the time required for the formation of the complex I and the complex II varies depending on properties of analytes A, the affinity substance α and the affinity substance β, the reaction may be properly carried out for several seconds to several hours, depending on their properties.

In the HPLC used for separating the complex I, the complex II and free affinity substance α in the process-1 of this invention, any apparatus can be used without any particular problem so long as it is usually used in the analysis field and has a constant flow rate. But needless to say, as a packing used in a column for separation, various packings should be properly chosen depending on the difference in properties among the complex I, the complex II and the free affinity substance α. For example, when the molecular weight of the complex II is about 1.2 times or more, preferably 1.5 times or more, more preferably 2 times or more, the molecular weight of the complex I, and the molecular weight of the complex I is about 1.2 times or more, preferably 1.5 times or more, more preferably 2 times or more, the molecular weight of free affinity substance α, packings for gel filtration (gel chromatography) are suitable. When the isoelectric points of the complex I, the complex II and free affinity substance α are different from one another and each difference between the isoelectric points is 0.05 or more, preferably 0.2 or more, packings for ion exchange chromatography or isoelectric focusing are suitable. When the complex I, the complex II and free affinity substance α are clearly different from one another in hydrophobicity, packings for hydrophobic chromatography or reversed phase chromatography, hydroxyapatite, or the like is suitable.

A solvent (an eluent) used for separating the complex I, the complex II and free affinity substance α by HPLC is not critical so long as it neither dissociates analyte A from the formed complexes I and II, nor takes the property detectable by some method away from the affinity substance α contained in the complex I and the complex II or away from the detectable substance of the affinity substance α. Usually, as the solvent, there is preferably used any of buffer solutions which are used in conventional methods such as EIA, RIA, FIA, affinity chromatography, etc. Preferable specific examples of the solvent are buffer solutions having a pH of 2 to 10 prepared by properly choosing, depending on properties of the complex I, the complex II and free affinity substance α, the following materials, followed by addition and mixing: for example, buffers such as phosphates, acetates, citrates, Good's buffers, tris(hydroxymethyl)-aminomethane, and the like; salts such as sodium chloride, potassium chloride, ammonium sulfate, and the like; organic solvents such as methanol, ethanol, isopropanol, acetonitrile, tetrahydrofuran, and the like; and surfactants.

In the process-1 of this invention, the amount of the affinity substance α contained in each of the complexes I and II separated by HPLC is measured by a predetermined method on the basis of the property detectable by some method of the affinity substance α or the detectable substance of affinity substance α. For example, when said property is an enzyme activity, the measurement is carried out according to a conventional method of EIA, for example, the method described in Tsunehiro Kitagawa, Toshio Nanbara, Akio Tsuji, and Eiji Ishikawa "Koso Men-eki Sokuteiho", an extra issue No. 31 of Tanpakushitsu Kakusan Koso, pp. 51–63, KYORITSU-SHUPPAN Ltd., published on Sep. 10, 1987, etc. When the detectable substance is a radioisotope, the measurement is carried out according to a conventional method of RIA by properly choosing and using a measuring instrument such as GM counter, liquid scintilation counter, well-type counter, counter for HPLC, or the like, depending on the kind and intensity of a radiation emitted by said radioisotope (see, for example, Yuichi Yamamura "Ikagaku Jikken Koza Vo. 8" 1st ed., NAKAYAMA-SHOTEN Ltd. 1971). When said property is fluorescence-emitting properties, the measurement is carried out according to a conventional method of FIA using a measuring instrument such as fluorometer, for example, the method described in Akira Kawano "Zusetsu Keikokotai" 1st ed., Soft Science, Inc., 1983, etc. When said property is luminescence-emitting properties, the measurement is carried out according to a conventional method using a measuring instrument such as photon counter, for example, the method described in Tsunehiro Kitagawa, Toshio Nanbara, Akio Tsuji and Eiji Ishikawa "Koso Men-eki Sokuteiho", an extra issue No. 31 of Tanpakushitsu Kakusan Koso, pp. 252-263, KYORITSU-SHUPPAN Ltd., published on Sep. 10, 1987, etc. When said property is ultraviolet-light-absorbing properties, the measurement is carried out by a conventional method using a measuring instrument such as spectrophotometer. When the detectable substance is a substance having properties as spin, the measurement is carried out according to a conventional method using an electron spin resonance apparatus, for example, the method described in Tsunehiro Kitagawa, Toshio Nanbara, Akio Tsuji and Eiji Ishikawa "Koso Men-eki Sokuteiho" an extra issue No. 31 of Tanpakushitsu Kakusan Koso, pp. 264-271, KYORITSU-SHUPPAN Ltd., published on Sep. 10, 1987, etc.

In the process-1 of this invention, for the measurement after the separation by HPLC, there is preferably employed the method comprising introducing an effluent from a column of HPLC into a detection section as its is, and directly measuring the amount of the affinity substance α contained in each of the complex I and the complex II in the effluent, which method is described, for example, in Shoji Hara and Akio Tsuji "Newest Liquid Chromatography" 1st ed., pp. 92-104, NANZANDO Ltd., published on Feb. 1, 1978. The reason is that this method permits rapid measurement. In this case, when the property detectable by some method of the affinity substance α or the detectable substance of affinity substance α is, for example, an enzyme activity, a reaction section of so-called post column method, in which a reagent for measuring the enzyme activity is added to the effluent to react therewith, should of course be provided between the column of HPLC and the detection section. As the reagent for measuring the enzyme activity which is used in the reaction section when said property of the affinity substance α or the detectable substance is the enzyme activity, there may be used a reagent prepared by a conventional method, for example, a method based on the content of Tsunehiro Kitagawa, Toshio Nanbara, Akio Tsuji and Eiji Ishikawa "Koso Men-eki Sokuteiho" an extra issue No. 31 of Tanpakushitsu Kakusan Koso, pp. 51-63, KYORITSU-SHUPPAN Ltd., published on Sep. 10, 1987, or there may be properly chosen and used a reagent of a commercially available kit for clinical examination. Also when said property of the affinity substance α or the detectable substance is other than enzyme activity, a suitable reaction section may be used between the column of HPLC and the detection section in order to add and react a predetermined reagent for the purpose of increasing the detection sensitivity. When the affinity substance β is labeled with the same detectable substance as the affinity substance α has, the amount of the affinity substance β in the complex II can of course also be measured by measuring the amount of the affinity substance α in each complex.

In the process-1 of this invention, when an antibody or antibodies are used as the substance having affinity for all of analytes A which is used as the affinity substance α or for preparation of the affinity substance α, and/or the affinity substance β, it is also possible to use the antibody or antibodies after digesting the same properly with an enzyme such as pepsin or papain into F(ab')$_2$, Fab' or Fab, depending on purposes. In particular, digestion into Fab' is advantageous in that Fab' can easily be labeled with a detectable substance. When the antibody or antibodies are used in the form of Fab' or Fab, the affinity substance α or the affinity substance β, or both can be bound to analyte(s) A for which each affinity substance has affinity, in a proportion of 1 molecule per molecule of the analyte(s) A (or in a proportion of 1 molecule per molecule of monomer in the case where the analyte(s) A is a dimer, a trimer or the like), so that the retention time of the complex I and the complex II in HPLC becomes substantially constant. Therefore, the employment of Fab' or Fab is preferable. Also in the case of using monoclonal antibody or antibodies having a property of binding only to one epitope site, the monoclonal antibody or antibodies can be bound to analyte(s) A in a proportion of 1 molecule per molecule of the analyte(s) A (or in a proportion of 1 molecule per molecule of monomer in the case where the analyte(s) A is a dimer, a trimer or the like), so that the retention time of the complex I and the complex II in HPLC becomes substantially constant. Therefore, the employment of the monoclonal antibody or antibodies is preferable. Needless to say, also in this case, the monoclonal antibody or antibodies may be used after digestion into Fab' or Fab.

As the antibody or antibodies used as the substance having affinity for all of the analytes A which is used as the affinity substance α or for preparation of the affinity substance α, and/or the affinity substance β in the process-1 of this invention, there may be used either polyclonal antibodies prepared by immunizing animals such as horse, cattle, sheep, rabbit, goat, rat, mouse, etc. with analyte(s) A according to a conventional method, for example, the method described in Tadashi Matsuhashi et al. "Men-ekigaku Jikken Nyumon" 2nd ed., GAKKAI-SHUPPAN CENTER Ltd., 1981, etc., or monoclonal antibodies produced by Hybridomas obtained by fusing cells from a tumor line of mouse together with mouse spleen cells previously immunized with analyte(s) A according to the conventional method, i.e., the cell fusion method established by G. Köhler and C. Milstein (Nature, 256, 495, 1975). These polyclonal and/or monoclonal antibodies may be used singly or in proper combination of two or more thereof.

Figure 5:
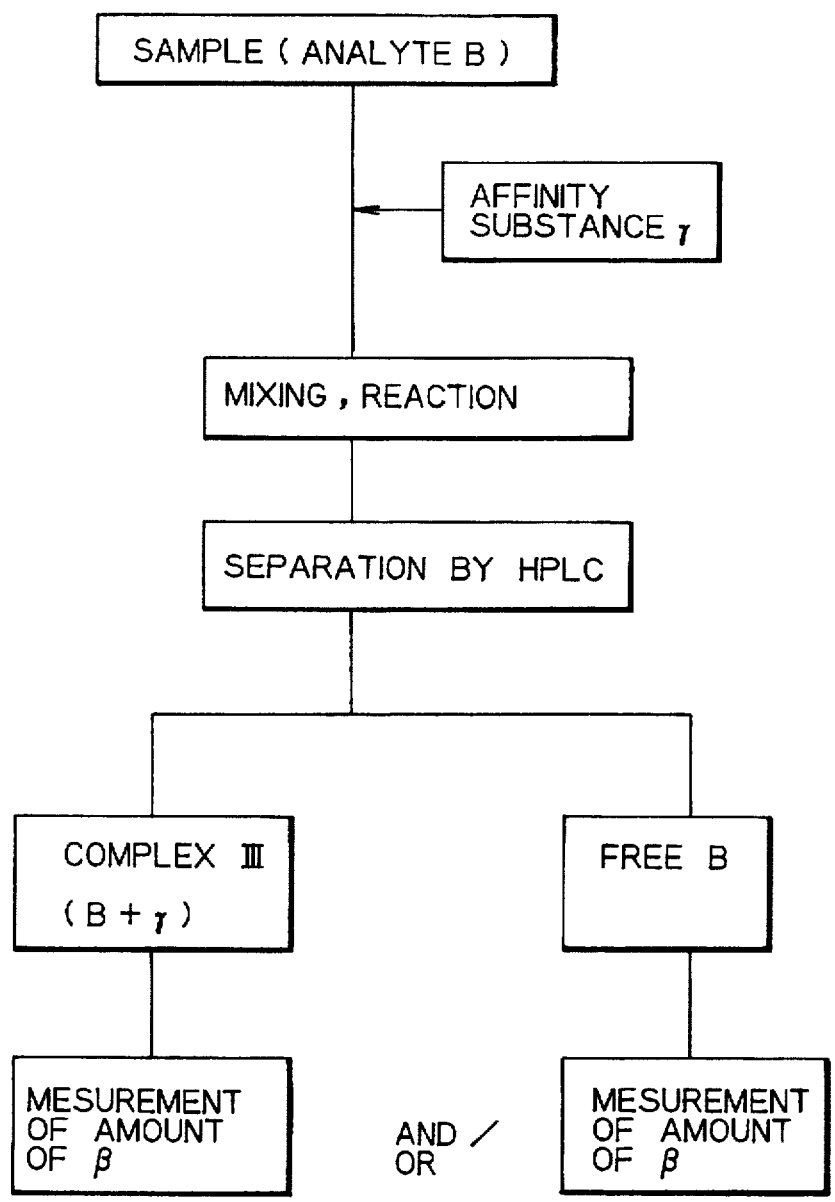

The process-2 of this invetnion is practised, for example, as shown in FIG. 5, as follows.

First, a sample derived from a living body which contains analytes B is reacted with an affinity substance γ, if necessary, by their addition to and mixing in a suitable buffer solution, to form a complex III. The complex III is then separated from free analyte(s) B by HPLC using a column packed with a predetermined packing. Subsequently, the amount of the analyte(s) B contained in the separated complex III or the amount of free analyte(s) B, or both, are determined by a measuring method suitable for properties of the analytes B. Thus, the amount of any of the analytes B in the sample can be determined.

Analytes B which can be measured by the process-2 of this invention are not critical so long as they are per se measurable (detectable) by some method and there exists an affinity substance γ, i.e., a substance which can form a stable complex with at least one of the analytes B by a high affinity between the substance and the analyte(s) B but does not bind to at least one of the other analytes B. Typical examples of the analytes B are enzymes and the like which are contained in samples derived from living bodies, for example, body fluids such as serum, blood, plasma, urine and the like, lymphocytes, hemocytes, and various cells. More specific examples of the analytes B are enzymes such as amylase, alkaline phosphatase, acid phosphatase, γ-glutamyltransferase (γ-GTP), lipase, creatine kinase (CK), lactate dehydrogenase (LDH), glutamic-oxaloacetic transaminase (GOT), glutamic-pyruvic transaminase (GPT), renin, protein kinases (PK), tyrosine kinase, and the like.

The affinity substance γ for the analytes B which is used in the process-2 of this invention is not critical so long as it can form a stable complex with at least one of the analytes B by a high affinity between the affinity substance γ and the analyte(s) B but does not bind to at least one of the other analytes B. The affinity substance γ includes, for example, antibodies against specific partial structures or antigenic determinants of substances having antigenicity (including haptens); lectins having affinity for sugar chains having a specific structure, such as concanavalin A, *Lens culinaris* lectin, *Phaseolus vulgaris* lectin, *Datura stramonium* agglutinin lectin, *Aleuria aurantia* lectin, *Ricinus communis* lectin, *Arackis hypogaea* lectin, *Triticum vulgaris* lectin and the like; and inhibitors for enzymes such as amylase, creatin kinase (CK), glutamic-oxaloacetic transaminase (GOT) and the like.

As the detectable chemical characteristic of the analytes B in the process-2, there can be exemplified enzyme activities, fluorescence-emitting properties, luminescence-emitting properties, and ultraviolet-light-absorbing properties.

More specific examples of combinations of the above analyte B and affinity substance γ are as shown in Table 2.

TABLE 2

| Analyte B | Affinity substance γ |
|---|---|
| Enzymes | Antibodies |
| Enzymes | Lectins |
| Enzymes | Inhibitors |

In the process-2 of this invention, the reaction conditions for reacting the analyte(s) B with the affinity substance γ to form the complex III are not critical so long as the reaction conditions do not change properties of the analytes B and the affinity substance γ. The reaction is carried out usually under reaction conditions employed for forming a complex or the like in a conventional method, for example, EIA, RIA, FIA or affinity chromatography. For example, when a buffer solution is used in the reaction, as the buffer and other reagents, those used in the above conventional methods may be properly chosen.

In the process-2 of this invention, the concentration of the affinity substance γ used for forming the complex III is not critical and may be properly determined depending on values at which the limit of measurement of the analytes B and the measurement sensitivity for the analytes B are set, respectively. As the affinity substance γ, employment of one substance is usually sufficient, though if necessary, a combination of two or more substances may be used. In this case, when there is used a combination of two or more affinity substances γ which bind to different sites, respectively, on optional analyte(s) B, the molecular weight of the resulting complex III is consequently increased and its isoelectric point is also varied in some cases. Therefore, the separation of the complex III from free analyte(s) B becomes easier, so that the precision of measurement can be improved. In addition, in the case of, for example, analytes B which are in the form of a mixture of X', Y' and Z', combined use of, for instance, an affinity substance γ for X' and an affinity substance γ for Y' makes it possible to separate and measure X', Y' and Z' at the same time.

In the process-2 of this invention, although the pH of the reaction is not critical so long as it does not inhibit the formation of the complex III, it is usually 2 to 10, preferably 5 to 9. Although the temperature of the reaction is also not critical so long as it does not inhibit the formation of the complex III, it is usually 0° to 50° C., preferably 20° to 40° C. As to the reaction time, since the time required for the formation of the complex III varies depending on properties of analytes B and the affinity substance γ, the reaction may be carried out for several seconds to several hours, depending on their properties.

In the HPLC used for separating the complex III from free analyte(s) B in the process-2 of this invention, any apparatus can be used without any particular problem so long as it is usually used in the analysis field and has a constant flow rate. But needless to say, as a packing used in a column for separation, various packings should be properly chosen depending on the difference in properties between the complex III and free analyte(s) B. For example, when the molecular weight of the complex III is about 1.2 times or more, preferably 1.5 times or more, more preferably 2 times or more, the molecular weight of free analyte(s) B, packings for gel filtration (gel chromatography) are suitable. When the difference between the isoelectric points of the complex III and free analyte(s) B is 0.05 or more, preferably 0.2 or more, packings for ion exchange chromatography or isoelectric focusing are suitable. When the complex III and free analyte(s) B are considerably different from each other in hydrophobicity, packings for hydrophobic chromatography or reverse phase chromatography, or hydroxyapatite is suitable.

A solvent (an eluent) used for separating the complex III from free analyte(s) B is not critical so long as it neither dissociates analyte A from the formed complex III nor takes the detectable chemical characteristic away from the analyte B contained in the complex III. Usually, as the solvent, there is preferably used any of buffer solutions which are used in conventional methods such as EIA, RIA, FIA, affinity chromatography, etc. Preferable specific examples of the solvent are buffer solutions having a pH of 2 to 10 prepared by properly choosing, depending on properties of the complex III and free analyte(s) B, the following materials, followed by addition and mixing: for example, buffers such as phosphates, acetates, citrates, Good's buffers, tris (hydroxymethyl)aminomethane, and the like; salts such as sodium chloride, potassium chloride, ammonium sulfate, and the like; organic solvents such as methanol, ethanol, isopropanol, acetonitrile, tetrahydrofuran, and the like; and surfactants.

In the process-2 of this invention, the analyte(s) B contained in the complex III separated by HPLC or free analyte (s) B is measured by a predetermined method, depending on the kind of the detectable chemical characteristic of analytes B. For example, when the analytes B are enzymes, the measurement is carried out according to a conventional method of EIA, for example, the method described in Tsunehiro Kitagawa, Toshio Nanbara, Akio Tsuji, and Eiji Ishikawa "Koso Men-eki Sokuteiho", an extra issue No. 31 of Tanpakushitsu Kakusan Koso, pp. 51–63, KYORITSU-SHUPPAN Ltd., published on Sep. 10, 1987, etc. When the analytes B are substances which can emit fluorescence, the measurement is carried out according to a conventional method of FIA using a measuring instrument such as fluorometer, for example, the method described in Akira Kawao "Zusetsu Keikokotai" 1st ed., Soft Science Inc., 1983, etc. When the analytes B are luminescent substances, the measurement is carried out according to a conventional method using a measuring instrument such as photon counter, for example, the method described in Tsunehiro Kitagawa, Toshio Nanbara, Akio Tsuji and Eiji Ishikawa "Koso Meneki Sokuteiho", an extra issue No. 31 of Tanpakushitsu Kakusan Koso, pp. 252–263, KYORITSU- SHUPPAN Ltd., published on Sep. 10, 1987, etc. When the analytes B are substances which can absorb an ultraviolet light, the measurement is carried out by a conventional method using a measuring instrument such as spectrophotometer.

In the process-2 of this invention, for the measurement after the separation by HPLC, there is preferably employed the method comprising introducing an effluent from a column of HPLC into a detection section as it is, and directly measuring the amount of the analyte(s) B contained in the complex III in the effluent or the amount of free analyte(s) B in the effluent, which method is described, for example, in Shoji Hara and Akio Tsuji "Newest Liquid Chromatography" 1st ed., pp. 92–104, NANZANDO Ltd., published on Feb. 1, 1978. The reason is that this method permits rapid measurement. In this case, when the analytes B are, for example, enzymes, a reaction section of so-called post column method, in which a reagent for measuring enzyme activity is added to the effluent to react therewith, should of course be provided between the column of HPLC and the detection section. As the reagent for measuring enzyme activity which is used in the reaction section when the analytes B are enzymes, there may be used a reagent prepared by a conventional method, for example, a method based on the content of Tsunehiro Kitagawa, Toshio Nanbara, Akio Tsuji and Eiji Ishikawa "Koso Men-eki Sokuteiho" an extra issue No. 31 of Tanpakushitsu Kakusan Koso, pp. 51–63, KYORITSU-SHUPPAN Ltd., published on Sep. 10, 1987, etc., or there may be properly chosen and used a reagent of a commercially available kit for clinical examination. Also when the analytes B are other than enzymes, a suitable reaction section may be used between the column of HPLC and the detection section in order to add and react a predetermined reagent for the purpose of increasing the detection sensitivity.

In the process-2 of this invention, when an antibody is used as the affinity substance γ, it is preferable to use the antibody after digesting it properly with an enzyme such as pepsin or papain into F(ab')$_2$, Fab' or Fab, depending on purposes. The reason is as follows. Immunoglobulin contained as antibody in usual antiserum is usually of IgG class. The molecular weight of IgG is about 150,000. When a complex III obtained by the reaction of IgG with analyte(s) B and free analyte(s) B are separated from each other, for example, on the gel chromatography principle, the separation is difficult unless the molecular weight of the analytes B is about 50,000 or more, and therefore the kind of the analytes B is inevitably limited. When an antibody to be used is digested with an enzyme into F(ab')$_2$ (molecular weight: about 100,000), Fab' (molecular weight: about 50,000) or Fab (molecular weight: about 50,000), substances having a molecular weight of 10,000 or more can be desirably used as the analytes B. When a monoclonal antibody having a property of binding only to one epitope site is used as the affinity substance γ, the affinity substance γ can be bound to he analyte(s) B in a proportion of 1 molecule per molecule of the analyte(s) B (or in a proportion of 1 molecule per molecule of monomer in the case where the analyte(s) B is a dimer, a trimer or the like), so that the retention time of the complex III in HPLC becomes substantially constant. Therefore, the employment of the monoclonal antibody is preferable. In this case, employment of Fab' or Fab obtained by digesting the monoclonal antibody has the advantages described above and hence is of course more preferable.

As the antibody used as the affinity substance γ in the process-2 of this invention, there may be used either polyclonal antibodies prepared by immunizing animals such as horse, cattle, sheep, rabbit, goat, rat, mouse, etc. with analyte(s) B according to a conventional method, for example, the method described in Tadashi Matsuhashi et al. "Men-ekigaku Jikken Nyumon" 2nd. ed, GAKKAI-SHUPPAN CENTER Ltd., 1981, etc., or monoclonal antibodies produced by Hybridomas obtained by fusing cells from a tumor line of mouse together with mouse spleen cells previously immunized with analyte(s) B, according to the conventional method, i.e., the cell fusion method established by G. Köhler and C. Milstein (Nature, 256, 495, 1975). These polyclonal and/or monoclonal antibodies may be used singly or in proper combination of two or more thereof.

As is clear from the above, according to the process-1 of this invention, the time required for the measurement is several minutes to several hours, and a necessary measuring procedure itself merely comprises mixing a sample containing analytes A, the affinity substance α and the affinity substance β, thereafter separating the complex I, the complex II and free affinity substance α from one another by HPLC, and measuring the amount of the affinity substance α in the complex I and/or the amount of the affinity substance α in the complex II. According to the process-2 of this invention, the time required for the measurement is several minutes to several hours, and a necessary measuring procedure itself merely comprises mixing a sample containing snalytes B with the affinity substance γ, thereafter separating the complex III from free analyte(s) B by HPLC, and measuring the amount of analyte(s) B in the complex III and/or the amount of free analyte(s) B. As is clear from these facts, the separating and measuring processes of this invention make it possible to carry out a desired measurement more easily and rapidly, as compared with conventional separating and measuring processes the purpose of which is the same as that of the processes of this invention.

This invention is more concretely explained below with reference to Examples, which are not by way of limitation but by way of illustration.

Example 1

Separation and measurement of human chorionic gonadotropins (hCG) different in sugar chain structure. [Eluent]

An eluent was prepared by dissolving 3.9 g of monosodium phosphate, 81 g of disodium phosphate dodecahydrate, 44 g of sodium chloride and 8.3 g of 3-(p-hydroxyphenyl)-propionic acid in deionized water, adjusting the resulting solution to pH 7.5 with a 1N NaOH solution, and then making up the total volume of 5 liters.

[Substrate solution]

A 20 mM solution of $H_2O_2$ was prepared as a substrate solution by diluting a 30% aqueous hydrogen peroxide solution with deionized water.

[Antibody solution]

Anti-hCG-β chain monoclonal antibody (available from Wako Pure Chemical Industries, Ltd.) was converted into Fab' by a conventional method. This Fab' was labeled with horseradish peroxidase (POD) by a conventional method and the thus obtained POD-labeled anti-hCG-β chain-Fab' was added to 50 mM phosphate buffer (pH 7.0, containing 150 mM sodium chloride) to adjust the protein concentration to 95 ng/ml, whereby an antibody solution was obtained.

[Lectin solution]

A lectin solution was prepared by adding Lens culinaris lectin (LCA-A) to 50 mM phosphate buffer (pH 7.0) to adjust the protein concentration to 1.5 mg/ml.

13

|Samples|

Solutions having a hCG concentration of 100, 200, 300, 400 or 500 mIU/ml were prepared by dissolving in deionized water each of commercially available hCG (derived from placental villi, available from Sigma Chemical Co.) and hCG derived from choriocarcinoma which had been purified from the serum of a patient with choriocarcinoma.

|Use conditions of HPLC|

The outline of a system was as given in FIG. 2.

Column and packing: 0.46 cm in diameter×60 cm, YMC-Diol-200 (a trade name, Yamamura Chemical Laboratories Co., Ltd.).

Flow rate: the eluent; 0.5 ml/min, the substrate solution; 0.05 ml/min.

Reaction section: 0.04 cm in diameter×900 cm (maintained at 40° C.).

Detection: Fluorescence was measured at an excitation wavelength of 320 nm and an emission wavelength of 404 nm.

|Measuring procedure|

After 40 μl of the antibody solution, 40 μl of the lectin solution and 20 μl of each sample were mixed and then allowed to stand at 30° C. for 30 minutes, 20 μl of the mixture was analyzed by HPLC.

[Results]

As a result of the analysis by HPLC, it was found that the POD-labeled anti-hCG-β chain-Fab' was eluted after 12.5 minutes, a complex of the POD-labeled anti-hCG-β chain-Fab' and hCG derived from placental villi (complex I) after 11.0 minutes, and a complex of the POD-labeled anti-hCG-β chain-Fab', LCA-A and hCG derived from choriocarcinoma (complex II) after 10.2 minutes. As is clear from these results, the hCG's different in sugar chain structure can be separated from each other by using the POD-labeled anti-hCG-β chain-Fab' and LCA-A as affinity substance α and affinity substance β, respectively.

Example 2

Separation and measurement of hCG and thyroid stimulating hormone (TSH).

[Eluent]

The same as in Example 1.

|Substrate solution|

The same as in Example 1.

[Antibody solution 1]

Anti-hCG-α chain monoclonal antibody (available from Wako Pure Chemical Industries, Ltd.) was converted into Fab' by a conventional method. This Fab' was labeled with horseradish peroxidase (POD) by a conventional method and the thus obtained POD-labeled anti-hCG-α chain-Fab' was added to 50 mM phosphate buffer (pH 7.0, containing 150 mM sodium chloride) to adjust the protein concentration to 70 ng/ml, whereby antibody solution 1 was obtained.

[Antibody solution 2]

Antibody solution 2 was prepared by adding anti-hCG-β chain monoclonal antibody (available from Wako Pure Chemical Industries, Ltd.) to 50 mM phosphate buffer (pH 7.5, containing 150 mM NaCl) to adjust the protein concentration to 950 μg/ml.

|Hormone solutions|

Hormone solutions were prepared by dissolving commercially available hCG (derived from placental villi, available from Sigma Chemical Co.) and TSH (available from UCB Bioproducts S.A.) in 50 mM phosphate buffer (pH 7.5, containing 150 mM NaCl) to adjust the concentration of each of them to 0.04, 0.08, 0.12, 0.16 or 0.20 nM.

14

|Use conditions of HPLC|

The outline of a system was the same as in FIG. 2.

Column and packing: 0.46 cm in diameter (φ)×60 cm, YMC-Diol-200 (a trade name, Yamamura Chemical Laboratories co., Ltd.)

Flow rate: the eluent: 0.5 ml/min, the substrate solution: 0.05 ml/min.

Reaction section: 0.04φ×900 cm (maintained at 55° C.).

Detection: Fluorescence was measured at an excitation wavelength of 320 nm and an emission wavelength of 404 nm.

|Measuring procedure|

After 40 μl of antibody solution 1, 20 μl of each hormone solution and 40 μl of antibody solution 2 were mixed and then allowed to stand at 30° C. for 30 minutes, 15 μl of the mixture was analyzed by HPLC.

|Results|

As a result of the analysis by HPLC, it was found that the POD-labeled anti-hCG-α chain-Fab' was eluted after 12.5 minutes, a complex of the POD-labeled anti-hCG-α chain-Fab' and TSH (complex I) after 11.7 minutes, and a complex of the POD-labeled anti-hCG-α chain-Fab', anti-hCG-β chain monoclonal antibody and hCG (complex II) after 10.2 minutes. As is clear from these results, hCG and TSH can be separated from each other by using the POD-labeled anti-hCG-α chain-Fab' and anti-hCG-62 chain monoclonal antibody as affinity substance α and affinity substance β, respectively.

Figure 1:
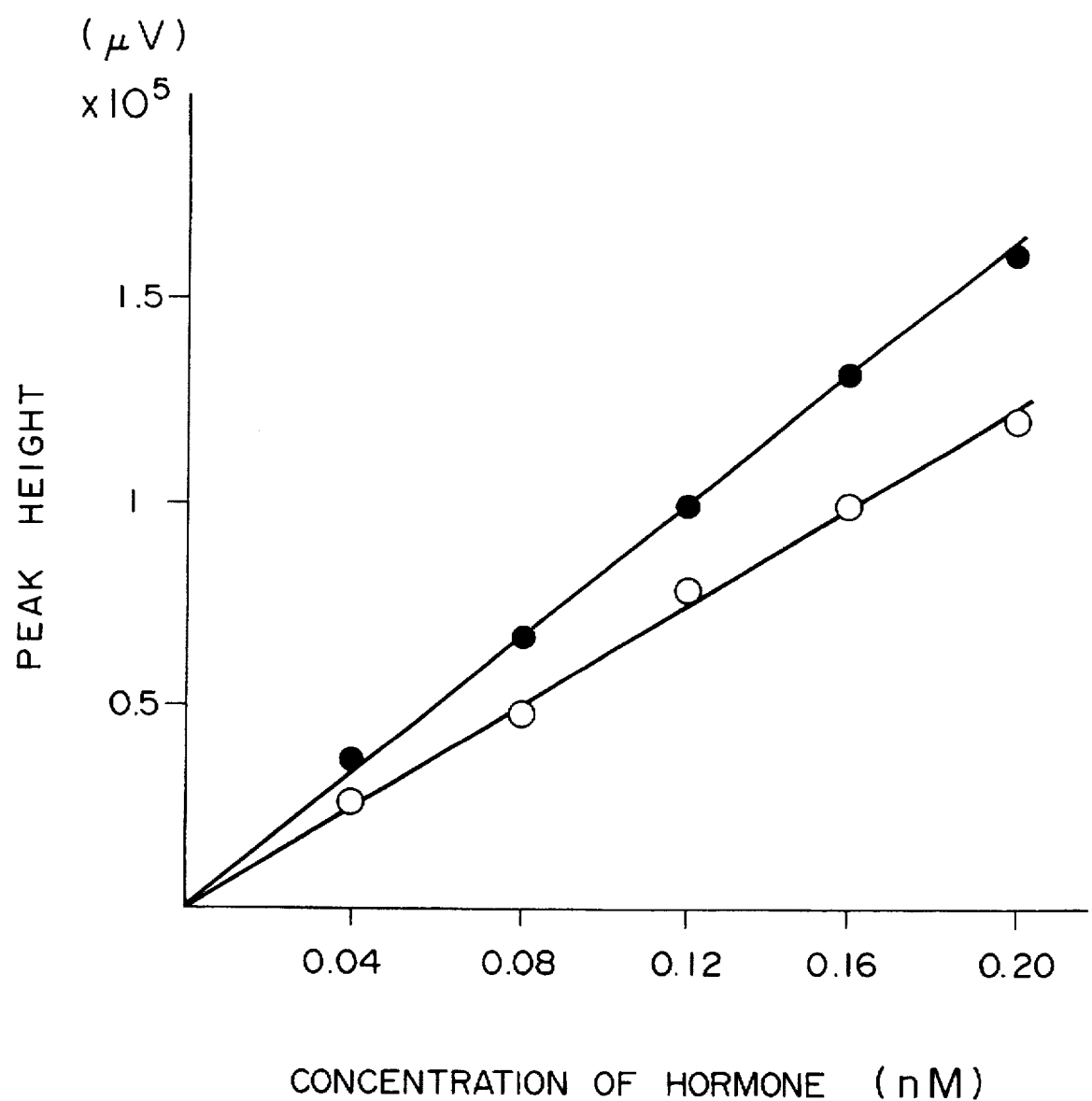
FIG. 1 shows a calibration curve obtained in Example 2.

FIG. 1 shows calibration curves showing the relationship between the hCG concentration (nM) or the TSH concentration (nM) of each sample and the peak height value (μV) of complex, which were obtained as a result of the analysis by HPLC. In FIG. 1, -○- shows a calibration curve for hCG, and -●- a calibration cruve for TSH.

Example 3

Separation and measurement of hCG, luteinizing hormone (LH) and thyroid stimulating hormone (TSH).

[Eluent]

The same as in Example 1.

|Substrate solution|

The same as in Example 1.

[Antibody solution 1]

The same as in Example 2.

[Antibody solution 2]

Antibody solution 2 was prepared by treating each of anti-hCG-β chain monoclonal antibody (available from Wako Pure Chemical Industries Ltd.) and anti-LH-β chain monoclonal antibody (available from Bioclone Australia Pty. Ltd.) into Fab by a conventional method, and adding these Fab's to 50 mM phosphate buffer (pH 7.5, containing 150 mM NaCl) to adjust the concentration of each protein to 2 μg/ml.

[Hormone solution]

A hormone solution was prepared by dissolving commerically available hCG (derived from placental villi, available from Sigma Chemical Co.), LH (available from UCB Bioproducts S.A.) and TSH (available from UCB Bioproducts S.A.) in 50 mM phosphate buffer (pH 7.5, containing 150 mM NaCl) to adjust concentration of each of them to 1 mM.

|Operating conditions of HPLC|

The outline of a system was the same as in FIG. 2.

Column and packing: 0.46×60 cm, YMC-Diol-200 (a trade name, Yamamura Chemical Laboratories Co., Ltd.).

Flow rate: the eluent; 0.5 ml/min, the substrate solution; 0.05 ml/min.

Reaction section: 0.04φ×900 cm (maintained at 55° C.).

Detection: Fluorescence was measured at an excitation wavelength of 320 nm and an emission wavelength of 404 nm.

|Measuring procedure|

After 40 μl of antibody solution 1, 30 μl of the hormone solution and 40 μl of antibody solution 2 were mixed and then allowed to stand at 30° C. for 30 minutes, 15 μl of the mixture was analyzed by HPLC.

|Results|

As a result of the analysis the HPLC, it was found that the POD-labeled anti-hCG-α chain-Fab' was eluted to show a peak after 12.5 minutes, a complex of the POD-labeled anti-hCG-α chain-Fab', the anti-hCG-β chain-Fab and hCG after 10.0 minutes, a complex of the POD-labeled anti-hCG-α chain-Fab', the anti-LH-β chain-Fab and LH after 11.0 minutes, and a complex of the POD-labeled hCG-α chain-Fab' and TSH after 11.9 minutes.

As is clear from these results, each hormone in a sample containing hCG, LH and TSH can be quantitatively determined by the separating and measuring process of this invention.

Comparative Example 1

|Eluent|

The same as in Example 1.

|Antibody solution 1|

The same as in Example 1.

|Hormone solution|

The same as in Example 3.

|Use conditions of HPLC|

The same as in Example 3.

|Measuring procedure|

After 40 μl of antibody solution 1, 30 μl of the hormone solution and 40 μl of 50 mM phosphate buffer (pH 7.5, containing 150 mM NaCl) were mixed and then allowed to stand at 30° C. for 30 minutes, 15 μl of the mixture was analyzed by HPLC.

|Results|

As a result of the analysis by HPLC, only a broad peak was observed besides a peak due to the POD-labeled anti-HCG-α chain-Fab' which was observed after 12.5 minutes, and there could not be identified none of peaks due to a complex of the POD-labeled anti-hCG-α chain-Fab' and hCG, a complex of the POD-labeled anti-hCG-α chain-Fab' and LH, and a complex of the POD-labeled anti-hCG-α chain-Fab' and TSH, respectively.

As is clear from these results, hCG, LH and TSH cannot be separated and detected by using the POD-labeled anti-hCG-α chain-Fab' alone.

Example 4

Separation and measurement of α-amylase isozymes.

|Eluent|

As an eluent, there was used 75 mM N,N-bis(2-hydroxyethyl)-2-aminoethanesulfonic acid (BES)-NaOH buffer (pH 7.6) containing 20 mM NaCl and 2 mM CaCl$_2$.

|Substrate solution|

A substrate solution was prepared by dissolving p-nitrophenyl benzyl-α-maltopentaoside, α-glucocidase and glucoamylase in the aforesaid eluent to adjust their concentrations to 14 mg/ml, 150 μ/ml and 300 μ/ml, respectively.

|Antibody solution|

An antibody solution was prepared by adding anti-human salivary α-amylase (mouse) monoclonal antibody (available from Wako Pure Chemical Industries, Ltd.) to the aforesaid eluent to adjust the protein concentration to 0.5 mg/ml.

|Samples|

Solutions prepared by properly diluting human serum with physiological saline were used as samples.

|Use conditions of HPLC|

The outline of a system was the same as in FIG. 2.

Column and packing: 0.75φ×30 cm, TSK gel G 2000SW (a trade name, Tosoh Ltd.).

Flow rate: the eluent; 1.0 ml/min, the substrate solution; 0.1 ml/min.

Reaction section: 0.04φ×900 cm (maintained at 37° C.).

Detection: Absorbance at 405 nm was measured.

|Measuring procedure|

After 300 μl of the antibody solution and 30 μl of each sample were mixed and then incubated at 37° C. for 30 minutes, 50 μl of the mixture was analyzed by HPLC.

|Results|

As a result of the analysis by HPLC, two peaks due to α-amylase were observed, indicating that salivary α-amylase and pancreatic α-amylase can be separated from each other.

The above procedure was repeated except for using samples prepared by properly adding pancreas α-amylase to physiological saline, and there was prepared a calibration curve showing the relationship between the peak area value obtained and the activity value of pancreatic α-amylase.

Figure 3:
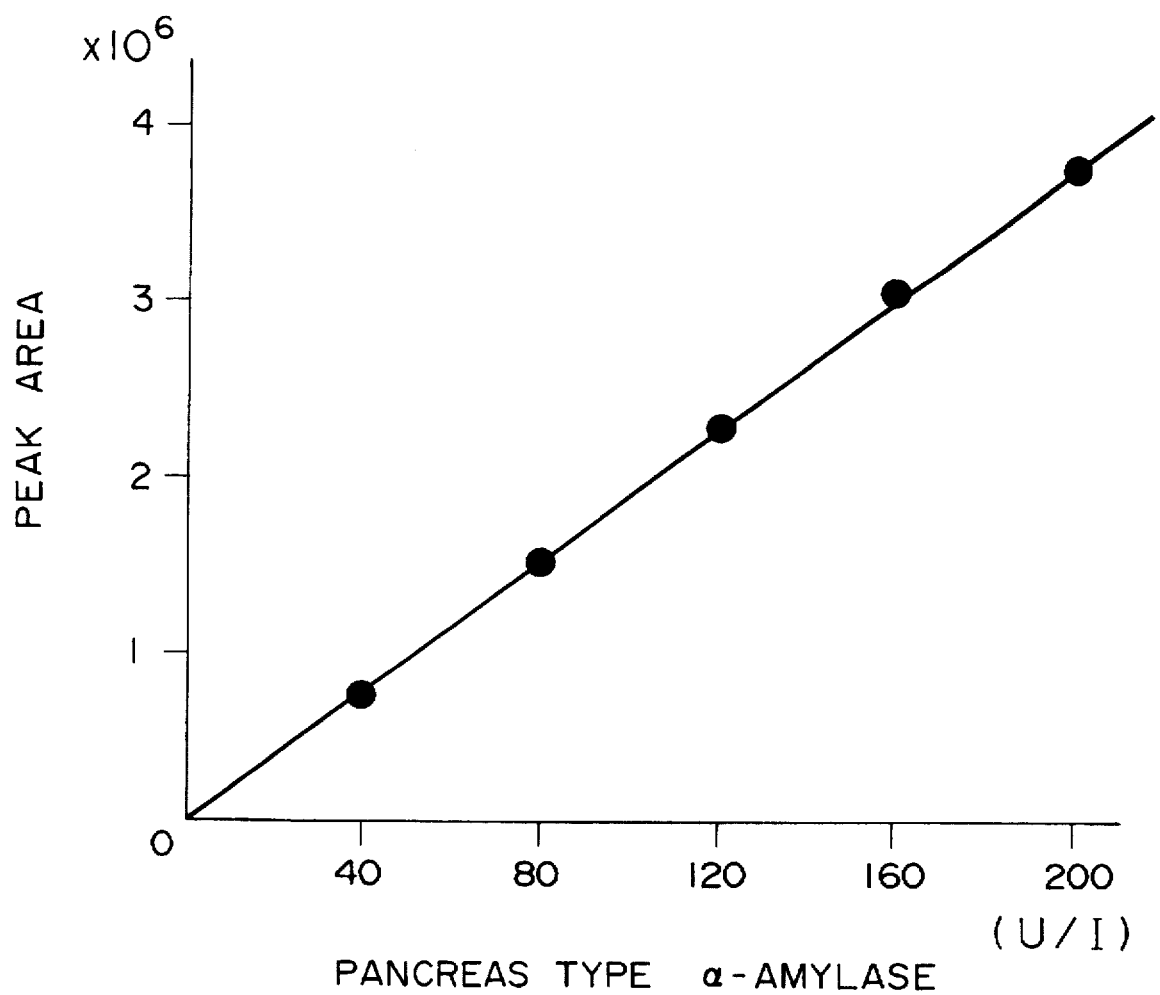
FIG. 3 shows a calibration curve obtained in Example 4.

The result obtained is shown in FIG. 3. The calibration curve shown in FIG. 3 was obtained by plotting peak area value on the axis of ordinate corresponding to individual pancreatic α-amylase activity value (u/liter) on the axis of abscissa.

As is clear from FIG. 3, the calibration curve starts from the zero point and shows good linearity.

Example 5

Separation and measurement of γ-glutamyltransferase (γ-GTP) isozymes.

|Eluent|

As an eluent, there was used 0.1M tris(hydroxymethyl) aminomethane-HCl buffer (pH 8.1) containing 70 mM glycylglycine, 0.15M NaCl and 2 mM EDTA.

|Lectin solution|

A lectin solution was prepared by dissolving Lens culinaris lectin (LCA-A) in 50 mM 2-(N-morpholino)-ethanesulfonic acid (MES) buffer (pH 7.0) to a concentration of 3 mg/ml.

|Substrate solution|

A substrate solution was prepared by dissolving γ-glutamyl-7-amido-4-methylcoumarin in the aforesaid eluent to a concentration of 0.4 mM.

|Sample|

Fresh human serum was used as a sample.

|Use conditions of HPLC|

The outline of a system was the same as in FIG. 2.

Column and packing: 0.94φ×25 cm, Zorbax GF-250 (a trade name, E. I. du Pont de Nemours & Co.).

Flow rate: the eluent; 1.0 ml/min, the substrate solution; 0.5 ml/min.

Reaction section: 0.04φ×900 cm (maintained at 40° C.).

Detection: Fluorescence was measured at an excitation wavelength of 395 nm and an emission wavelength of 480 nm.

|Measuring procedure|

After 20 μl of the lectin solution and 20 μl of the sample were mixed and then incubated at 37° C. for 30 minutes, 15 μl of the mixture was analyzed by HPLC.

|Results|

As a result of the analysis by HPLC, it was found that a complex of γ-GTP having a sugar chain with fucose and LCA-A was eluted after 5.8 minutes and γ-GTP having no sugar chain with fucose after 11.3 minutes.

Example 6

Separation and measurement of lactate dehydrogenase (LDH) isozymes.

|Eluent|

As an eluent, there was used 10 mM tris(hydroxymethyl) aminomethane-HCl buffer (pH 8.7) containing 0.15M NaCl.

|Antibody solution|

An antibody solution was prepared by diluting a commercially available anti-human LDH (H-subunit) monoclonal antibody solution (available from ICN Biomedicals, Inc.) in 10 times with the aforesaid eluent.

|Substrate solution|

As a substrate solution, there was used 500 mM tris (hydroxymethyl)aminomethane-HCl buffer (pH 8.7) containing 385 mM L-lactic acid and 22 mM $\beta$-NAD$^+$.

|Sample|

Fresh human serum was used as a sample.

|Use conditions of HPLC|

The outline of a system was the same as in FIG. 2.

Column and packing: 0.8$\phi$×30 cm, YMC-Diol-300 (a trade name, Yamamura Chemical Laboratories Co., Ltd.).

Flow rate: the eluent; 1.0 ml/min, the substrate solution; 0.1 ml/min.

Reaction section: 0.04$\phi$×900 cm (maintained at 37° C.).

Detection: Fluorescence was measured at an excitation wavelength of 370 nm and an emission wavelength of 465 nm.

|Measuring procedure|

After 120 µl of the antibody solution and 30 µl of the sample were mixed and then incubated at 30° C. for 60 minutes, 100 µl of the mixture was analyzed by HPLC.

|Results|

As a result of the analysis by HPLC, it was found that $LDH_1$ was eluted after 11.1 minutes, $LDH_2$ after 10.1 minutes, $LDH_3$ after 9.3 minutes, $LDH_4$ after 8.9 minutes, and $LDH_5$ after 8.3 minutes.

As described above, this invention provides a process which makes it possible to separate and measure analytes to be measured in samples derived from living bodies, rapidly and easily with high precision on the basis of chemical and/or physical properties of the analytes. According to the process-1 of this invention, the time required for the measurement is several minutes to several hours, and a necessary measuring procedure itself merely comprises mixing a sample containing analytes A, the affinity substance α and the affinity substance β, thereafter separating the complex I, the complex II and free afinity substance α from one another by HPLC, and measuring the amount of the affinity substance α in the complex I and/or the amount of the affinity substance α in the complex II. According to the process-2 of this invention, the time required for the measurement is several minutes to several hours, and a necessary measuring procedure itself merely comprises mixing a sample containing analytes B with the affinity substance γ, thereafter separating the complex III from free analyte(s) B by HPLC, and measuring the amount of analyte B in the complex III and/or the amount of the free analyte(s) B. Therefore, the processes of this invention make it possible to carry out a desired measurement more easily and rapidly, as compared with conventional separating and measuring processes the purpose of which is the same as that of the processes of this invention. This invention is markedly effective in this point and contributes greatly to the art.

What is claimed is:

1. A process for separating and simultaneously measuring the total of and specific components of analytes having similar physiological activities or similar structures contained in a bodily fluid which comprises:

mixing in a buffer solution a sample of a bodily fluid containing two or more analytes, which have (a) similar physiological activities or (b) similar structures and different physiological activities with a first affinity substance which binds to all of the analytes and has itself a detectable property or has been labeled with a detectable substance, and a second affinity substance which binds to at least one of the analytes but does not bind to at least one of the other analytes, reacting the analytes with the first and second affinity substances in said buffer solution, separating a first complex consisting of the analytes bound to the first affinity substance, a second complex of the analytes bound to the first and second affinity substances, and residual unbound first affinity substance from one another by high pressure liquid chromatography, separately preparing linear calibration curves showing the values of the detectable property of the first affinity substance corresponding to the concentrations of the analytes in the first and second complexes from a series of incrementally differing samples having known concentrations of the analytes, and determining the amount in the effluent from the high-pressure liquid chromatography of the first affinity substance in the first complex and/or the amount of the first affinity substance in the second complex, by comparison with the linear calibration curve, thereby simultaneously measuring (1) the total amount of said two or more analytes, (2) the amount of the specific analyte or analytes bound to the second affinity substances and (3) the amount of the analyte or analytes other that the specific analyte or analytes.

2. A process according to claim 1, wherein the separation of the first complex, the second complex and the unreacted first affinity substance is carried out by high pressure liquid chromatography using a column packed with a packing selected from the group consisting of a packing for gel filtration, a packing for ion-exchange chromatography, a packing for hydrophobic chromatography, a packing for isoelectric focusing, a packing for reversed phase chromatography and hydroxyapatite.

3. A process according to claim 1, wherein the analytes are enzymes.

4. A process according to claim 1, wherein the analytes are tumor associated antigens.

5. A process according to claim 1, wherein the analytes are substances having a sugar chain.

6. A process according to claim 1, wherein the first affinity substance is a labeled or non-labeled antibody, or a labeled or non-labeled lectin; and the second affinity substance is an antibody or a lectin.

7. A process according to claim 6, wherein the antibody of the first affinity substance is a monoclonal antibody.

8. A process according to claim 6, wherein the lectin is concanavalin A, *Lens culinaris* lectin, *Phaseolus vulgaris* lectin, *Datura stramonium* agglutinin lectin, *Aleuria aurantia* lectin, *Ricinus communis* lectin, *Arachis hypogaea* lectin or *Triticeum vulgaris* lectin.

9. A process according to claim 6 wherein the antibody of the second affinity substance is a monoclonal antibody.

* * * * *